United States Patent
Zhang et al.

(10) Patent No.: US 11,547,790 B2
(45) Date of Patent: Jan. 10, 2023

(54) INTRAVENOUS FLUID BAG HOLDER

(71) Applicant: Austin Hardware & Supply Inc., Lee's Summit, MO (US)

(72) Inventors: Daye Zhang, Suwanee, GA (US); Robert Walden, Buford, GA (US)

(73) Assignee: Austin Hardware & Supply, Inc., Lee's Summit, MO (US)

( * ) Notice: Subject to any disclaimer, the term of this patent is extended or adjusted under 35 U.S.C. 154(b) by 180 days.

(21) Appl. No.: 16/881,349

(22) Filed: May 22, 2020

(65) Prior Publication Data

US 2021/0361857 A1    Nov. 25, 2021

(51) Int. Cl.
*A61M 5/14*    (2006.01)

(52) U.S. Cl.
CPC ........ *A61M 5/1417* (2013.01); *A61M 5/1415* (2013.01); *A61M 2209/082* (2013.01)

(58) Field of Classification Search
CPC .......... F16B 45/02; F16B 45/06; F16B 45/00; B60R 7/08; B60R 2011/0028; A61M 5/1417; A61M 5/1415; A61M 2209/082; A61G 3/001; F16M 13/027; F16M 13/02; E05D 11/08; E05D 11/082; E05D 11/084; E05D 2011/085; E05D 11/081; Y10T 24/45408; F16L 3/237; A47G 25/0607
USPC ...... 248/95, 227.1, 304–306, 308, 322, 339; 224/311; 24/599.4
See application file for complete search history.

(56) References Cited

U.S. PATENT DOCUMENTS

| | | | | |
|---|---|---|---|---|
| 3,432,129 | A * | 3/1969 | Santucci | F16L 3/237 248/69 |
| D244,585 | S * | 6/1977 | Jonsson | D8/367 |
| 4,044,983 | A * | 8/1977 | Francis | A61M 5/1415 248/318 |
| 4,367,859 | A * | 1/1983 | Lamon | A61G 3/001 248/318 |
| 5,613,381 | A * | 3/1997 | Savage | E05B 75/00 70/18 |
| 5,940,943 | A * | 8/1999 | Kloster | F16B 45/02 24/DIG. 37 |
| 5,984,250 | A * | 11/1999 | Connor | A47G 25/0607 294/82.19 |
| 6,338,463 | B1 * | 1/2002 | Babitz | A47G 25/0607 248/306 |
| 10,066,659 | B2 * | 9/2018 | Osaki | A47G 25/0607 |
| 10,295,087 | B2 * | 5/2019 | Chouinard | F16L 3/237 |

(Continued)

OTHER PUBLICATIONS

Fix My Ambulance; SelectTech Inc; IV Hooks & Holders; Jul. 31, 2012; https://www.fixmyambulance.com/category-s/1884.htm (Year: 2012).*

(Continued)

*Primary Examiner* — Ingrid M Weinhold
(74) *Attorney, Agent, or Firm* — Polsinelli PC (57) ABSTRACT

An intravenous (IV) fluid bag hanger is described for use in an ambulance or other emergency vehicle. A handle is configured to pivot or rotate between storage and deployed positions. The fluid bag hanger includes a double-sided carabiner. The double-sided carabiner includes a first holding region and a second holding region to hold one or more intravenous fluid bags. The double-sided carabiner forms a hub between the first holding region and the second holding region. An axle of the handle rotates in the hub.

21 Claims, 5 Drawing Sheets

(56) References Cited

U.S. PATENT DOCUMENTS

| | | | |
|---|---|---|---|
| 10,793,077 B2* | 10/2020 | Villacres Mesias | B60R 7/08 |
| 11,054,063 B2* | 7/2021 | Ratzlaff | H02G 3/32 |
| 2016/0108953 A1* | 4/2016 | Osaki | F16B 45/00 |
| | | | 248/305 |
| 2018/0274699 A1* | 9/2018 | Ratzlaff | F16L 3/1075 |

OTHER PUBLICATIONS

Zeropole Paramedic IV Bag Hanger; Sav-A-Jake; Dec. 9, 2010; https://www.savajake.com/Zeropole-Paramedic-IV-Bag-Hanger-Red_p_1082.html (Year: 2010).*

Perko Snap Type Fender Hook; Jul. 27, 2017; https://www.walmart.com/ip/Perko-1309DP0CHR-Snap-Type-Fender-Hook/34051408 (Year: 2017).*

Ambulance Ceiling IV Hook Portable IV Stand; New Fellow; Nov. 11, 2018; http://www.emsstretcher.com/sale-3166074-ambulance-ceiling-iv-hook-portable-iv-stand-with-15cm-length.html (Year: 2018).*

Cast Products, Inc. "IV Hangers" 2008; 3 pages.

* cited by examiner

INTRAVENOUS FLUID BAG HOLDER

FIELD OF THE INVENTION

The present invention relates to an intravenous (IV) fluid bag hanger.

BACKGROUND OF INVENTION

Prior intravenous fluid bag hangers for ambulances have mounting structures with a depth that requires excessive roof material thickness and consume valuable headspace or protrude too much from the ceiling of the ambulance. Such structures may prove to be an obstacle or annoyance to ambulance workers.

Additionally, prior intravenous bag hangers for ambulances may be difficult to operate or require a two-handed motion by a user in order to hang the intravenous bags.

SUMMARY OF THE INVENTION

An intravenous fluid bag hanger is described for use in an ambulance or other emergency vehicle. A handle is configured to pivot or rotate between storage and deployed positions. The fluid bag hanger includes a double-sided carabiner. The double-sided carabiner includes a first holding region and a second holding region to hold one or more intravenous fluid bags. The double-sided carabiner forms a hub between the first holding region and the second holding region. An axle of the handle rotates in the hub.

The intravenous fluid bag hanger includes a low-profile design or shallow mount design that fits into or protrudes from the ceiling of the ambulance or emergency vehicle. An intravenous fluid bag may be easily hung from the intravenous fluid bag hanger with a one-hand motion.

In one aspect, an intravenous fluid bag hanger includes a handle configured to pivot or rotate between storage and deployed position. The hanger includes a carabiner having a base portion. The base portion includes an arm. A closing member is pivotally engaged to an end of the arm of the base portion. The closing member is biased to a closed position to form a holding region configured to hold one or more intravenous fluid bags. A closing end of the closing member abuts or contacts an end of the central member. A distal portion of the end of the central member extends outward past a point of abutment or contact between the closing end of the closing member and the end of the central member. The closing end of the closing member abuts or contacts the end of the central member between the distal portion of the end and the central member. This distal portion provides a convenient target for the user to thread or insert a loop of an intravenous bag onto. This distal portion also provides a ramp, which directs the loop to contact the closing member in order to open the carabiner. The user may push the loop against the closing member in order to open the carabiner. The loop may be pulled over the distal portion and pulled along a length of the end of the central member and ultimately against the closing member, which may automatically open the closing member. Once the loop is passed the end of the closing member, the closing member may automatically close. This distal portion assists in providing a carabiner that may be easily opened with a one-hand motion. The user may pull the loop against the closing member to open the closing member. A two handed motion to open the closing member and to further hang the loop is not required.

In another aspect, an intravenous fluid bag hanger is described. The intravenous bag hanger includes a handle configured to pivot or rotate between storage and deployed positions. The intravenous bag hanger includes a double-sided carabiner having a base portion, and the base portion includes a first arm and a second arm. A first closing member of the double-sided carabiner is pivotally engaged to a first end of the first arm of the base portion. The first closing member forms a first holding region configured to hold one or more intravenous fluid bags. A closing end of the first closing member abuts or contacts a first end of a central member, and a distal portion of the first end of the central member extends outward past a point of abutment or contact between the closing end of the first closing member and the first end of the central member. A second closing member of the double-sided carabiner is pivotally engaged to a second end of the second arm of the base portion. The second closing member forms a second holding region configured to hold one or more intravenous fluid bags. A closing end of the second closing member abuts or contacts a second end of the central member. A distal portion of the second end of the central member extends outward past a point of abutment or contact between the closing end of the second closing member and the second end of the central member. The intravenous bag hanger includes the handle that rotates relative to the double-sided carabiner.

In another aspect, an intravenous fluid bag hanger is described. The intravenous bag hanger includes a housing. The intravenous bag hanger includes a handle comprising an axle. The handle is configured to pivot or rotate between storage and deployed positions with respect to the housing. The intravenous bag hanger includes a double-sided carabiner. The double-sided carbineer includes a base portion. The base portion is integral with a first arm and a second arm. A first closing member is pivotally engaged to a first end of the first arm of the base portion. The first closing member is biased to a closed position. A closing end of the first closing member abuts or contacts a first end of a central member. A second closing member is pivotally engaged to a second end of the second arm of the base portion. The second closing member is biased to a closed position. A closing end of the second closing member abuts or contacts a second end of the central member.

In another aspect, an intravenous fluid bag hanger is described. The intravenous bag hanger includes a housing. The intravenous bag hanger includes a handle comprising an axle. The handle is configured to pivot or rotate between storage and deployed positions with respect to the housing. The intravenous bag hanger includes a first carabiner configured to hold one or more intravenous fluid bags. The intravenous bag hanger includes a second carabiner configured to hold one or more intravenous fluid bags. The first and second carabiners form a hub between the first holding region and the second holding region, and the axle of the handle pivots or rotates in the hub.

In another aspect, an intravenous fluid bag hanger is described. The intravenous bag hanger includes a handle configured to pivot or rotate between storage and deployed positions. The intravenous bag hanger includes a carabiner. The carabiners include a base portion, and the base portion includes an arm. A closing member is pivotally engaged to an end of the arm of the base portion. The closing member is biased to a closed position to form a holding region configured to hold one or more intravenous fluid bags. A closing end of the closing member abuts or contacts an end of a central member, and a distal portion of the end of the central member extends outward past a point of abutment or contact between the closing end of the closing member and the end of the central member.

In another aspect, an intravenous fluid bag hanger is described. The intravenous fluid bag hanger includes a handle configured to pivot or rotate between storage and deployed positions. The intravenous bag hanger includes a double-sided carabiner. The double-sided carabiner including a first holding region and a second holding region to hold one or more intravenous fluid bags. The double-sided carabiner includes a base portion, and the base portion includes a first arm and a second arm. A first closing member is pivotally engaged to a first end of the first arm of the base portion, the first closing member is biased to a closed position, wherein a closing end of the first closing member abuts or contacts a first end of a central member. A second closing member is pivotally engaged to a second end of the second arm of the base portion. The second closing member is biased to a closed position. A closing end of the second closing member abuts or contacts a second end of the central member.

In another aspect, a method of hanging one or more intravenous fluid bags is described. The method includes directing an opening of one of the one or more intravenous fluid bags at a point of contact of between the closing member and the central member. The method includes pushing against the closing member to open the holding region. The method includes hanging the bag in the holding region.

In another aspect, a method of hanging one or more intravenous fluid bags is described. The method includes providing an intravenous fluid bag hanger having a carabiner, the carabiner includes a base portion, and the base portion includes an arm. The carabiner further includes a closing member that is pivotally engaged to an end of the arm of the base portion. The closing member is biased to a closed position to form a holding region configured to hold one or more intravenous fluid bags. A closing end of the closing member abuts or contacts an end of a central member, and a distal portion of the end of the central member extends outward past a point of abutment or contact between the closing end of the closing member and the end of the central member. The method further includes threading or inserting a loop of one of the one or more intravenous fluid bags onto the distal portion. The method further includes sliding the loop on the distal portion. The method further includes directing the loop to contact the closing member in order to open the carabiner. The method further includes hanging the bag in the holding region. The method further may further include securing the bag to a handle of the intravenous bag hanger.

In another aspect, a double-sided carabiner for hanging one or more intravenous fluid bags is described. The double-sided carabiner includes a base portion. The base portion includes a first arm and a second arm. A first closing member is pivotally engaged to a first end of the first arm of the base portion. The first closing member is biased to a closed position to form a first holding region configured to hold the one or more intravenous fluid bags. A closing end of the first closing member abuts or contacts a first end of a central member. A distal portion of the first end of the central member extends outward past a point of abutment or contact between the closing end of the first closing member and the first end of the central member. A second closing member is pivotally engaged to a second end of the second arm of the base portion. The second closing member is biased to a closed position to form a second holding region configured to hold the one or more intravenous fluid bags. A closing end of the second closing member abuts or contacts a second end of the central member. A distal portion of the second end of the central member extends outward past a point of abutment or contact between the closing end of the second closing member and the second end of the central member.

DETAILED DESCRIPTION OF THE INVENTION

An intravenous (IV) fluid bag hanger 10 is described. The bag hanger 10 may be mounted in the ceiling or other elevated location of an ambulance or other emergency vehicle. The bag hanger 10 includes a double-sided carabiner 300 for hanging or holding one or more intravenous bags 400. The bag hanger 10 includes a handle 100 configured to pivot or rotate between storage and deployed positions.

The bag hanger 10 allows for the medical or emergency personnel to hang the intravenous bag 400 using a single hand, as the user's single hand may hold the IV bag 400 while simultaneously opening the double-sided carabiner 300 by pushing against the double-sided carabiner 300 in order to hang the IV bag 400. Thus, the user may pull down the handle 100 with their single hand and easily hang the IV bag 400 by pushing against the double-sided carabiner 300 with their single hand.

In this aspect, the bag hanger 10 includes the handle 100 pivotally or rotatably mounted to a housing 200. The handle 100 may pivot or rotate between storage and deployed positions with respect to the housing 200. In the storage position, the handle 100 may pivot or rotate upward into a recess 210 of the housing 200. In the deployed position, the handle 100 may pivot or rotate downward. This provides for the handle 100 to be folded up and out of the way when not in use. In other aspects, the bag hanger 10 mounts to the ceiling or other structure of the ambulance without the housing 200.

The housing 200 includes a flange portion 220, which forms a perimeter of the housing 200. The flange portion 220 may include openings for fasteners to pass through the flange portion 220 in order for the fasteners to secure to the ceiling of the ambulance. The flange portion 220 transitions into sidewalls 230, which partially define the recess 210. The sidewalls 230 transition into a central wall 240.

In the aspect shown, the double-sided carabiner 300 is mounted to the central wall 240 of the housing 200. In this aspect, fasteners 242 pass through the housing 200 and secure to a base portion 305 of the double-sided carabiner 300.

Figure 4:
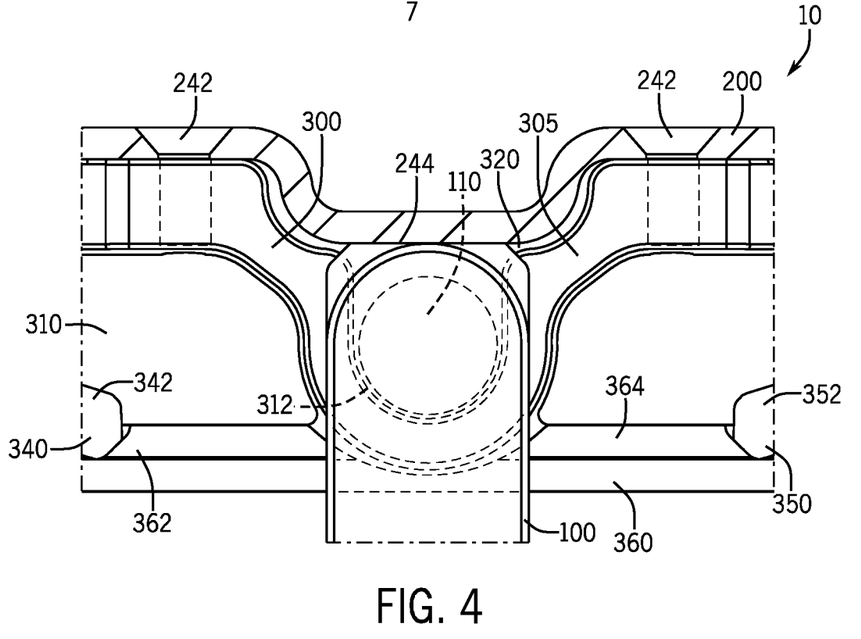
FIG. 4 is a detailed view of the axle of the bag hanger in the deployed position.

The double-sided carabiner 300 includes a first holding region 310 and a second holding region 315. Each of the first holding region 310 and the second holding region 315 may hang or hold one or more of the IV bags 400. The double-sided carabiner 300 forms a hub 320 between the first holding region 310 and the second holding region 315. The handle 100 is held by the hub 320. With reference to FIG. 4, the hub 320 forms a rounded or curved surface 312 that receives an axle 110 of the handle 100. The axle 110 pivots or rotates in the hub 320. The hub 320 may be formed as a bend or curve in the base portion 305.

Figure 1:
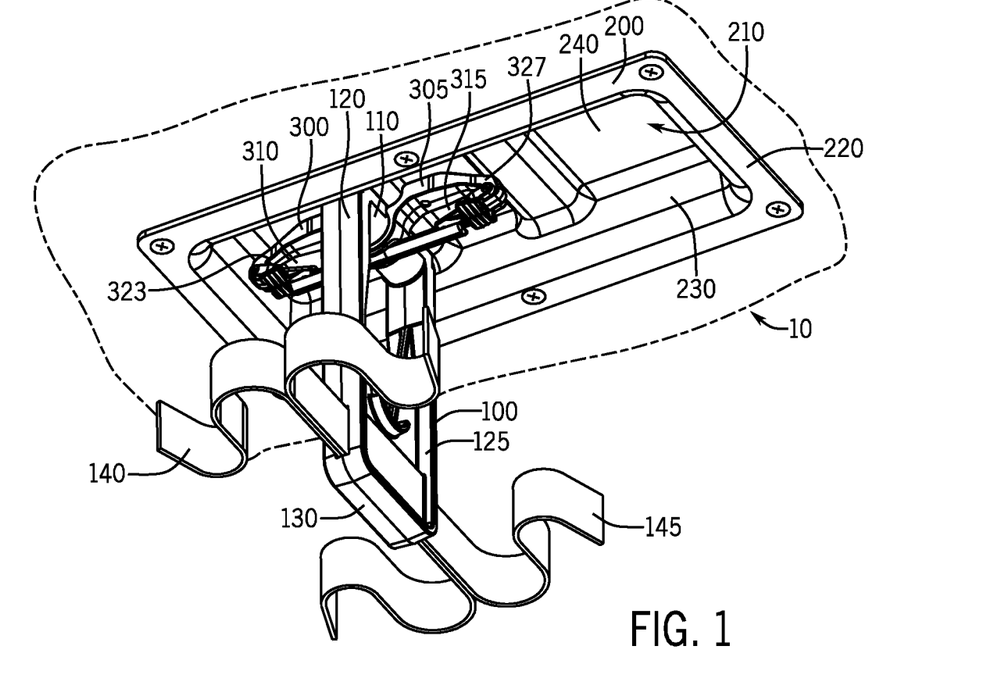
FIG. 1 is a perspective view of the bag hanger.
Figure 2:
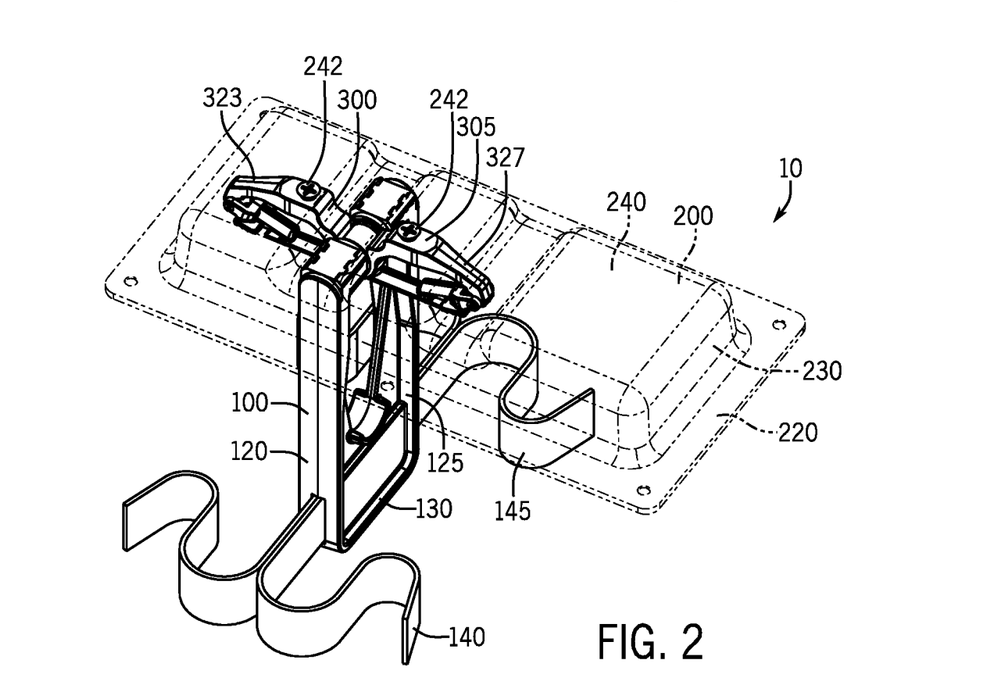
FIG. 2 is a perspective view of the bag hanger.

The handle 100 will now be described with reference to FIGS. 1 and 2. The handle 100 includes first and second elongate members 120 and 125 that join with both the axle 110 and a gripping portion 130. The gripping portion 130 is generally opposite of the axle 110. The handle 100 further includes first and second straps 140 and 145 that secure around the IV bags 400. The first and second straps 140 and 145 may include hook and loop fasteners, snaps, etc. to secure around the IV bags 400. The first and second straps 140 and 145 reduce movement or swinging of the IV bags 400 when the ambulance or emergency vehicle is moving.

The double-sided carabiner 300 includes the first holding region 310 and the second holding region 315. The double-sided carabiner 300 includes the base portion 305. The base portion 305 includes a first arm 323 and a second arm 327. The first arm 323 and the second arm 327 form opposing sides of the base portion 305. The first arm 323 and the second arm 327 angle downward from the central wall 240 of the housing 200. The first arm 323 and the second arm 327 are on opposite sides of the hub 320.

Figure 3:
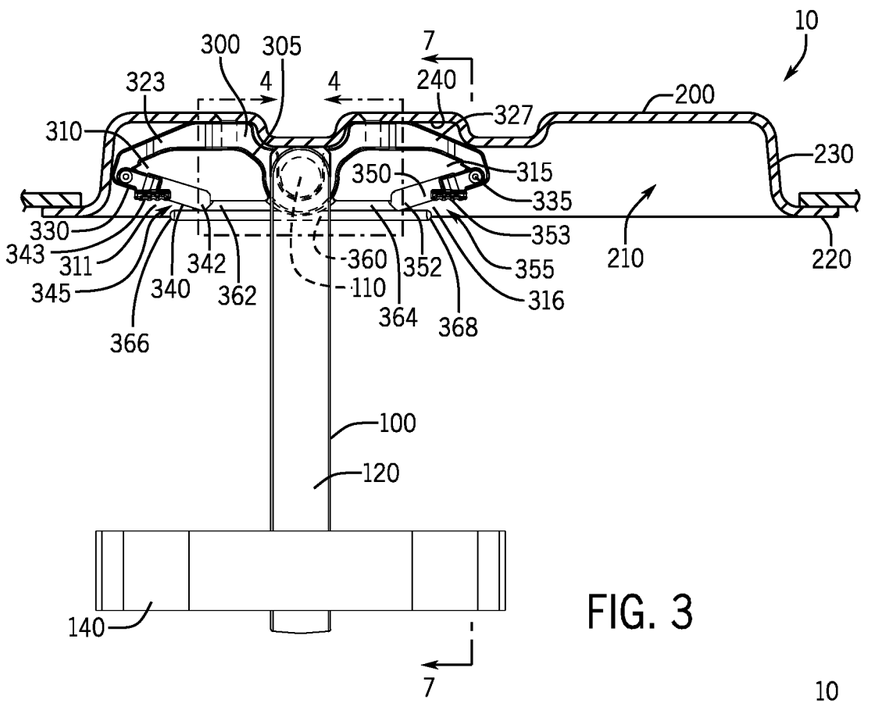
FIG. 3 is a side sectional view of the bag hanger.

With respect to FIG. 3, a first closing member 340 is pivotally engaged to a first end 330 of the first arm 323 of the base portion 305. The first closing member 340 is biased to a closed position, wherein a closing end 342 of the first closing member 340 abuts or contacts a first end 362 of a central member 360. A second closing member 350 is pivotally engaged to a second end 335 of the second arm 327 of the base portion 305. The second closing member 350 is biased to a closed position wherein a closing end 352 of the second closing member 350 abuts or contacts a second end 364 of the central member 360. In this aspect shown, the first end 362 and the second end 364 extend in opposite directions from the central member 360.

In the aspect shown, the closing end 342 of the first closing member 340 abuts or contacts the first end 362 of the central member 360 at an angle, and the first end 362 extends beyond a point of contact between the closing end 342 and the first end 362. As such, the first closing member 340 abuts or contacts the first end 362 of the central member 360 between a distal portion 366 of the first end 362 and the central member 360. This distal portion 366 extends past the point of abutment or contact between the closing end 342 and the first end 362. This arrangement between the first end 362 and the closing end 342 forms a catch area or receiving region 345 that provides a natural or obvious target for the user to hang a loop 410 of the IV bag 400. Once the user slides or threads the loop 410 onto the distal portion 366 of the first end 362, the loop 410 will naturally travel along the first end 362, push against the closing member 340 causing the closing member 340 to swing inward, and travel into the first holding region 310. After the user threads or slides the loop 410 onto the distal portion 366, the user can push or pull the loop 410 along the first end 362, which acts as a ramp leading to the closing member 340. The user may pull or push the loop 410 against the closing member 340 in order to open the closing member 340. Once the loop 410 is pulled or pushed past the closing end 342 and into the holding region 310, the closing member 340 may automatically swing closed to a locked position. This provides the user the ability to hang the IV bag 400 with a single motion or a one handed movement. The loop 410 may be pressed or pulled against the closing member 340 in order to automatically open the closing member 340.

Further, the extension of the first end 362 beyond a point of contact between the closing end 342 and the first end 362 provides additional security to prevent the unwanted opening of the closing member 340. When the IV bag 400 pulls against the first closing member 340, the first closing member 340 tightens further against the first end 362. Further, the first closing member 340 includes a pad 343 for pressing the first closing member 340 to the open position. The pad 343 may include a textured surface to provide a visual and tactile reminder that the user is to push on the first closing member 340 in this location. In this aspect, the pad 343 may be formed at an angle relative the remainder of the first closing member 340 to provide further direction or indication to the user that the pad 343 is to be pressed. The pad 343 may be formed as an integral portion of the first closing member 340.

In this aspect, the second closing member 350 and its closing end 352 abuts or contacts the second end 364 of the central member 360 in the same or similar manner as the first closing member 340 and the first end 362 and likewise forms a catch area or receiving region 355 and a pad 353 with the same or similar functions. The second end 364 of the central member 360 likewise forms a distal portion 368 that inserts into the loop 410 of the IV bag 400.

The hub 320 may be formed as a bend or curve in the base portion 305. The axle 110 may be held between the bend/curve and a lower surface 244 of the central wall 240.

The first closing member 340 pivots inward to an open position to open a first opening 311 of the first holding region 310, while the second closing member 350 pivots inward to an open position to open a second opening 316 of the second holding region 315. In certain aspects, the first and second closing members 340 and 350 are biased to their respective closed positions by spring tension or bias. The first and second closing members 340 and 350 automatically close, by the spring tension or bias, when released by the user. In other aspects, the first and second closing members 340 and 350 are not biased by a spring, and the first and second closing members 340 and 350 move to their respective closed positions by gravity or by weight of the IV bags 400.

The loops 410 of the IV bags 400 may slide into the first holding region 310 and/or the second holding region 315. In this aspect, the first and second closing members 340 and 350 both pivot inward toward the base portion 305, however, one of the first and second closing members 340 and 350 pivots in a clockwise direction, and the other of the first and second closing members 340 and 350 pivots in a counter-clockwise direction. In other aspects, the first and second closing members 340 and 350 pivot in the same direction.

As shown in FIG. 3, the first closing member 340 and the second closing member 350 angle toward the central member 360 in the closed position. The first closing member 340 and the second closing member 350 contact the central member 360 in the closed position. The central member includes a generally linear portion with its first end 362 and second end 364 generally oppositely disposed. The central member 360 may be integral with the hub 320 and the base portion 305. The first holding region 310 and the second holding region 315 are on opposite sides of the hub 320 of the double-sided carabiner 300. The central member 360 forms part of both of the first holding region 310 and the second holding region 315. In the closed position, the first closing member 340 and the second closing member 350 may angle toward the central member 360 at approximately 15 degrees to approximately 60 degrees. In the aspect shown in the FIG. 3, in the closed position, the first closing member 340 and the second closing member 350 angle toward the central member 360 at approximately 30 degrees.

The handle 100 may be formed from synthetic rubbers, natural rubbers, and similar materials. In this aspect, the handle 100 is formed from EPDM (Ethylene Propylene Diene Monomer), which provides a handle structure that will generally remain folded up in the storage position or will remain generally steady in the deployed position. The double-sided carabiner 300 may be formed by using cast aluminum or other alloys.

Figure 5:
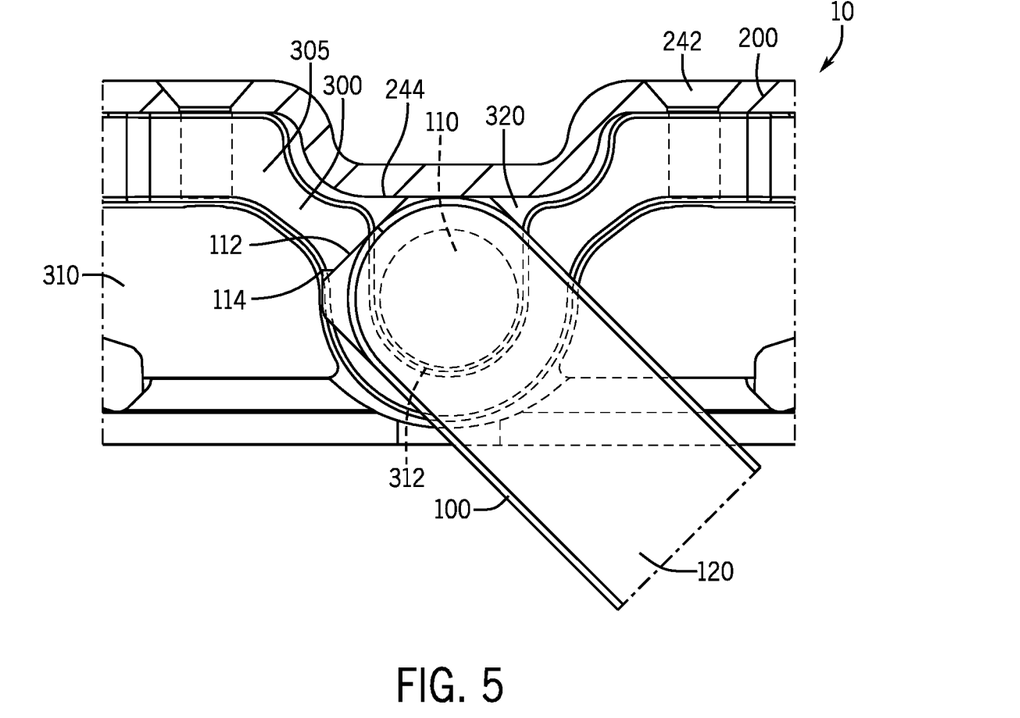
FIG. 5 is a detailed view of the axle of the bag hanger moving upward to the storage position.
Figure 6:
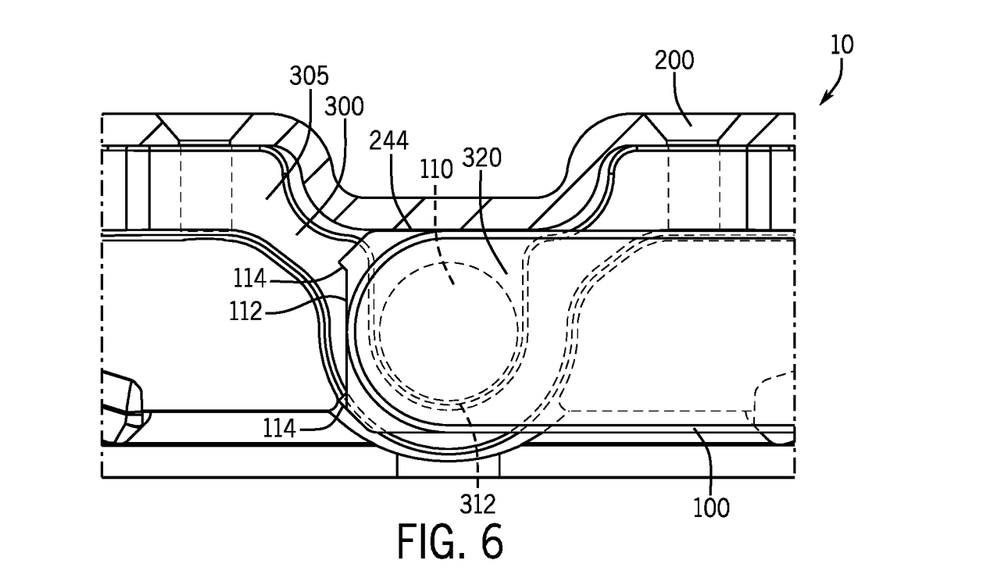
FIG. 6 is a detailed view of the axle of the bag hanger in the storage position.
Figure 7:
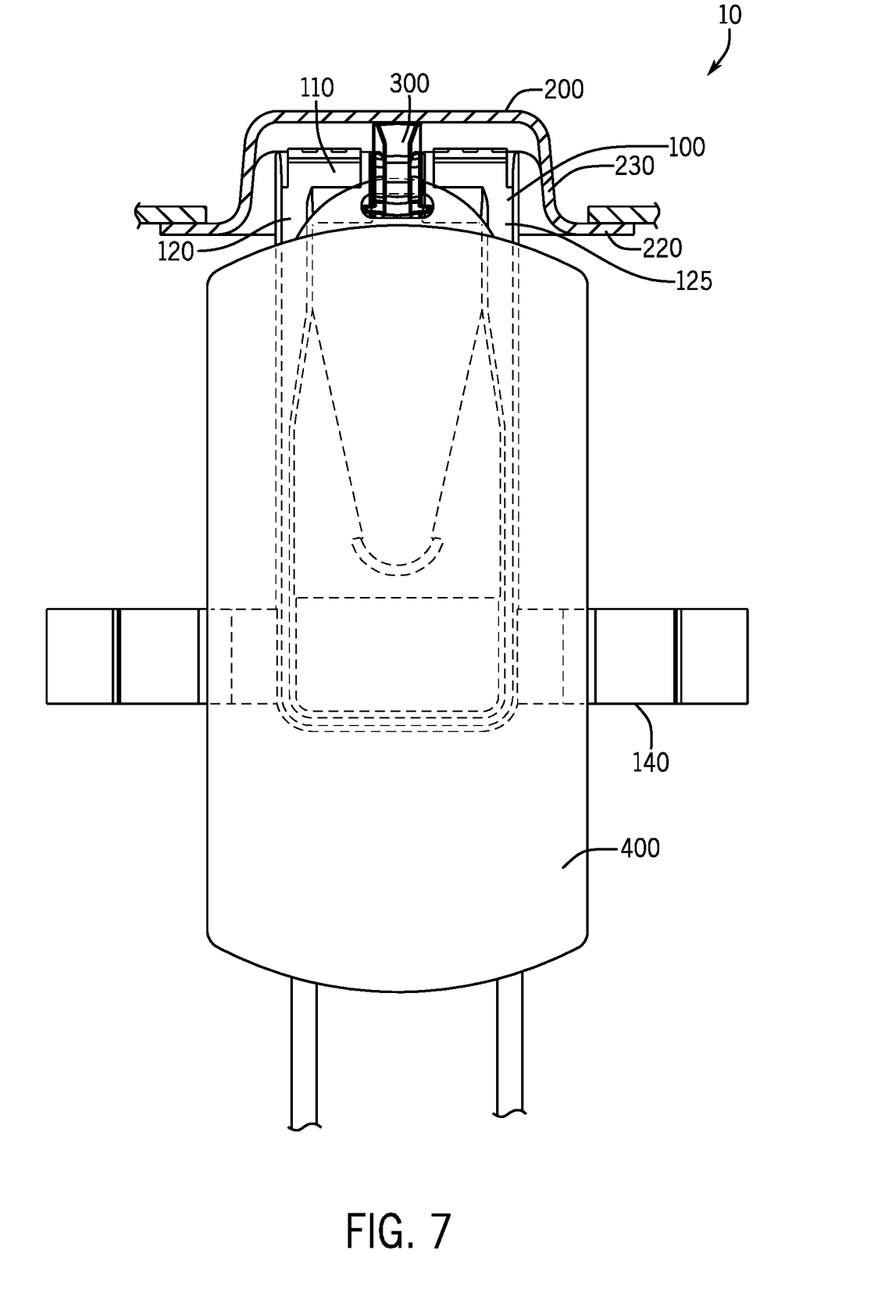
FIG. 7 is a side view of the bag hanger holding the intravenous bag.
Figure 8:
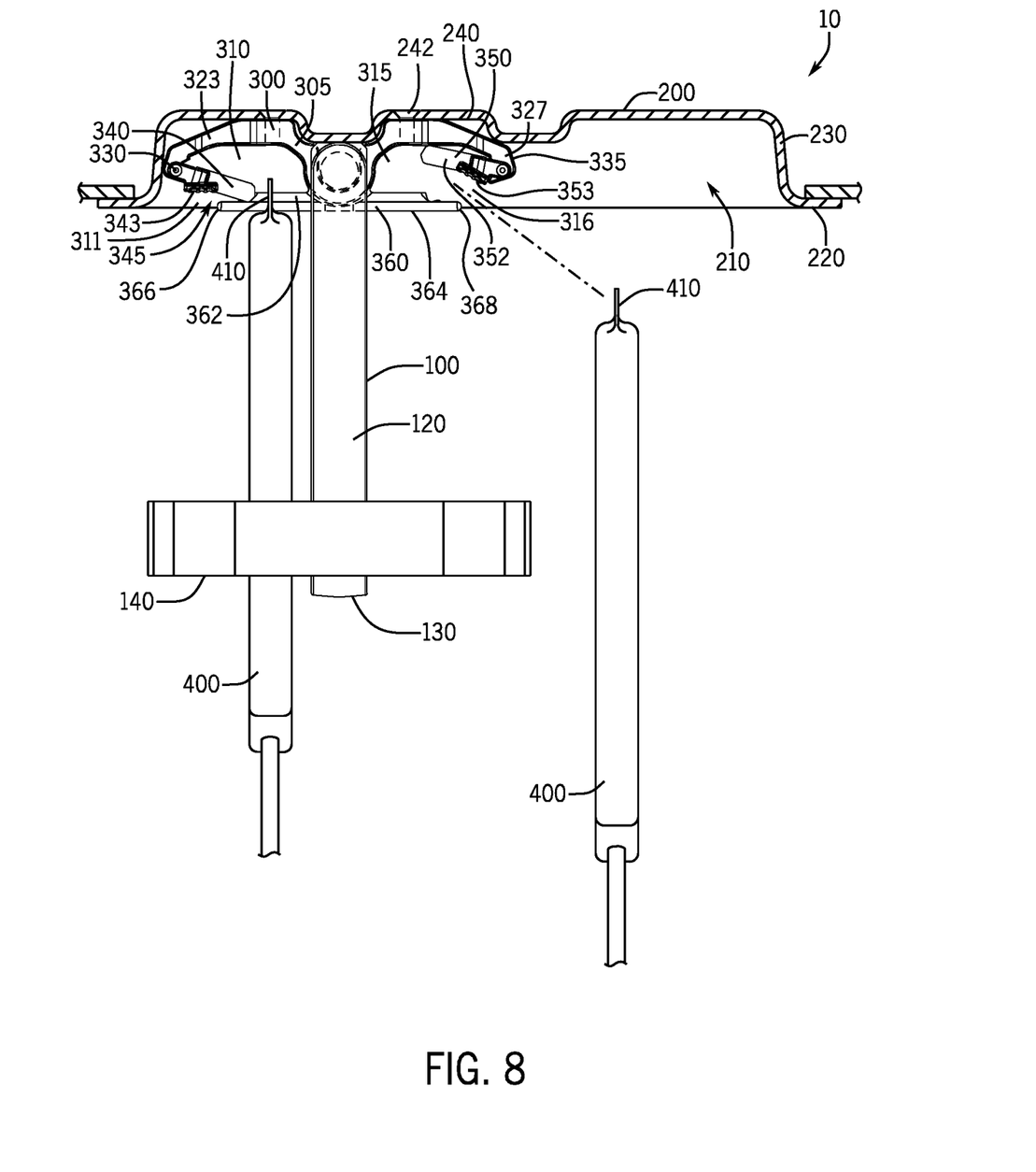
FIG. 8 is a side view of hanging the intravenous bag to the bag hanger.

As shown in FIGS. 4-6, a back side of the axle 110 includes a generally flat surface 112 with protuberances 114. In this aspect, the protuberances 114 are positioned on the outer sides of the axle 110. The protuberances 114 bias the handle 100 to the storage position, and the protuberances 114 further bias the handle 100 to remain generally steady in the deployed position. As shown in FIG. 5, the protuberances 114 crush or deform when sufficient rotating force is applied to the handle 100 to cause movement between the storage and deployed positions. However, the protuberances 114 bias the handle 100 to the storage position with sufficient strength to maintain the handle 100 in the storage position. Further, once moved to the deployed position, the protuberances 114 bias the handle 100 with sufficient strength to reduce a swinging movement of the handle 100 when the emergency vehicle is moving.

In other aspects, the base portion 305 of the double-sided carabiner 300 may be installed or mounted directly to the ceiling of the ambulance without using the housing 200. The hub 320 of the base portion 305 may receive the axle 110 of the handle 100 and rotatably hold the axle 110 against the ceiling. In additional aspects, other support members or mounting structures may be used to the mount the double-sided carabiner 300 to the ceiling of the ambulance.

In other aspects, a single carabiner may be mounted to housing 200 or mounted directly to the ceiling of the ambulance without using the housing 200. The single carabiner may include either half of the double-sided carabiner 300. For example, the single carabiner includes the closing end 342 of the first closing member 340 abutting or contacting the first end 362 of the central member 360 at an angle, and the first end 362 extends beyond a point of contact between the closing end 342 and the first end 362. Similarly, the first closing member 340 abuts or contacts the first end 362 of the central member 360 between a distal portion 366 of the first end 362 and the central member 360. This distal portion 366 extends past the point of abutment or contact between the closing end 342 and the first end 362. This arrangement between the first end 362 and the closing end 342 forms a catch area or receiving region 345 that provides a natural or obvious target for the user to hang a loop 410 of the IV bag 400 as well as providing the ramp function herein described. In other aspects, the bag hangers of the present disclosure may include three of the single carabiners described above. In other aspects, the bag hangers of the present disclosure may include one of the single carabiners described above in addition to the double-sided carabiner 300. In other aspects, the bag hangers of the present disclosure may include two of the double-sided carabiners 300 for hanging additional IV bags 400 and/or other medical supplies and equipment.

In other aspects, the double-sided carabiner 300 may be used without the handle 100. The double-sided carabiner 300 may be mounted to the housing 200 or mounted directly to the ceiling of the ambulance or other structure without using the handle 100.

In other aspects, the double-sided carabiner 300 may be used with a handle or other bag supporting structure that is fixed, i.e., non-rotating. In certain applications where headroom is not a factor, the double-sided carabiner 300 may be used with the fixed handle or other fixed bag supporting structure.

Although the bag hanger 10 has been described herein as being used in an ambulance or other emergency vehicle, the bag hanger 10 may be used in other mobile applications, such as medical busses, helicopters, planes, etc. Further, the bag hanger 10 may be used in other medical facilities, such as hospitals, operating rooms, patient rooms, clinics, portable medical structures, etc. As such, it should be understood that the disclosure is not limited to the particular aspects described herein, but that various changes and modifications may be made without departing from the spirit and scope of this novel concept as defined by the following claims. Further, many other advantages of applicant's disclosure will be apparent to those skilled in the art from the above descriptions and the claims below.

What is claimed is:

1. An intravenous fluid bag hanger, comprising:
a housing;
a handle configured to pivot or rotate between storage and deployed positions with respect to the housing;
a double-sided carabiner mounted to the housing;
the double-sided carabiner comprising:
a base portion, and the base portion includes a first arm and a second arm on opposite sides of the base portion, the first and the second arm angle downward from the base portion;
a first closing member is pivotally engaged to a first end of the first arm of the base portion to form a first holding region configured to hold one or more intravenous fluid bags, wherein a closing end of the first closing member abuts or contacts a first end of a central member, and a distal portion of the first end of the central member extends outward past a point of abutment or contact between the closing end of the first closing member and the first end of the central member,
a second closing member is pivotally engaged to a second end of the second arm of the base portion to form a second holding region configured to hold one or more intravenous fluid bags, wherein a closing end of the second closing member abuts or contacts a second end of the central member; and a distal portion of the second end of the central member extends outward past a point of abutment or contact between the closing end of the second closing member and the second end of the central member; and,
the handle rotates relative to the double-sided carabiner.

2. The intravenous fluid bag hanger according to claim 1, wherein the double-sided carabiner forms a hub between the first holding region and the second holding region, and the handle rotates in the hub.

3. The intravenous fluid bag hanger according to claim 2, wherein the hub forms a rounded or curved surface that receives an axle of the handle.

4. The intravenous fluid bag hanger according to claim 1, wherein the distal portion of the first end of the central member or the distal portion of the second end of the central member are configured to receive a loop of one of the one or more intravenous fluid bags.

5. The intravenous fluid bag hanger according to claim 4, wherein the distal portion of the first end of the central member provides a ramp to the first closing member or the distal portion of the second end of the central member provides a ramp to the second closing member.

6. The intravenous fluid bag hanger according to claim 1, wherein the handle includes first and second elongate members that join with both an upper portion of the handle forming an axle and a gripping portion of the handle, wherein the gripping portion is generally opposite of the axle.

7. The intravenous fluid bag hanger according to claim 1, wherein the first closing member and the second closing member angle toward and contact the central member in a closed position.

8. The intravenous fluid bag hanger according to claim 1, wherein an upper portion of the handle forms an axle, wherein a back side of the axle of the handle includes a generally flat surface with protuberances, wherein the protuberances crush or deform when sufficient rotating force is applied to the handle to cause movement from the storage position to the deployed position.

9. The intravenous fluid bag hanger according to claim 1, wherein the intravenous fluid bag hanger is configured to be mounted on an emergency vehicle, wherein an upper portion of the handle forms an axle, wherein a back side of the axle of the handle includes protuberances, wherein in the deployed position the protuberances bias the handle with sufficient strength to reduce a swinging movement of the handle when the emergency vehicle is moving.

10. The intravenous fluid bag hanger according to claim 1, wherein the double-sided carabiner receives an axle of the handle.

11. The intravenous fluid bag hanger according to claim 1, wherein the housing is configured to mount to a ceiling of an ambulance.

12. The intravenous fluid bag hanger according to claim 1, wherein the intravenous fluid bag hanger provides for one-handed operation by a user.

13. The intravenous fluid bag hanger according to claim 1, wherein the first closing member is biased to a closed position to form the first holding region, and the second closing member is biased to a closed position to form the second holding region.

14. The intravenous fluid bag hanger according to claim 1, wherein the first closing member pivots to open and close a first opening of the first holding region, and the second closing member pivots to open and close a second opening of the second holding region, and the first opening and the second opening face in opposite diagonal directions.

15. The intravenous fluid bag hanger according to claim 1, wherein the first closing member pivots to open and close a first opening of the first holding region, and the second closing member pivots to open and close a second opening of the second holding region, and the first opening and the second opening are within the housing and face in opposite diagonal directions.

16. The intravenous fluid bag hanger according to claim 1, wherein the first closing member pivots inward, in a clockwise direction, toward the base portion to open the first holding region, wherein the second closing member pivots inward in a counterclockwise direction toward the base portion to open the second holding region.

17. An intravenous fluid bag hanger, comprising:
a handle configured to pivot or rotate between storage and deployed positions;
a double-sided carabiner comprising:
a base portion, and the base portion includes a first arm and a second arm,
a first closing member is pivotally engaged to a first end of the first arm of the base portion to form a first holding region configured to hold one or more intravenous fluid bags, wherein a closing end of the first closing member abuts or contacts a first end of a central member, and a distal portion of the first end of the central member extends outward past a point of abutment or contact between the closing end of the first closing member and the first end of the central member,
a second closing member is pivotally engaged to a second end of the second arm of the base portion to form a second holding region configured to hold one or more intravenous fluid bags, wherein a closing end of the second closing member abuts or contacts a second end of the central member; and a distal portion of the second end of the central member extends outward past a point of abutment or contact between the closing end of the second closing member and the second end of the central member;
an upper portion of the handle forms an axle;
the handle rotates relative to the double-sided carabiner; and
wherein a back side of the axle of the handle includes a generally flat surface with protuberances.

18. The intravenous fluid bag hanger according to claim 17, wherein the protuberances are positioned on outer sides of the axle.

19. An intravenous fluid bag hanger, comprising:
a housing;
a handle comprising an axle, the handle configured to pivot or rotate between storage and deployed positions with respect to the housing;
a double-sided carabiner, the double-sided carabiner includes a base portion, the base portion integral with a first arm and a second arm;
the base portion forms a hub between the first arm and the second arm, the hub configured to receive the axle in a rotational engagement; and,
a first closing member is pivotally engaged to a first end of the first arm of the base portion, the first closing member is biased to a closed position, wherein a closing end of the first closing member abuts or contacts a first end of a central member, wherein a second closing member is pivotally engaged to a second end of the second arm of the base portion, and the second closing member is biased to a closed position, wherein a closing end of the second closing member abuts or contacts a second end of the central member.

20. The intravenous fluid bag hanger according to claim 19, wherein the first closing member and the second closing member angle toward the central member at approximately 15 degrees to approximately 60 degrees.

21. An intravenous fluid bag hanger, comprising:
a handle configured to pivot or rotate between storage and deployed positions;
a double-sided carabiner comprising:
a base portion, and the base portion includes a first arm and a second arm,
a first closing member is pivotally engaged to a first end of the first arm of the base portion to form a first holding region configured to hold one or more intravenous fluid bags, wherein a closing end of the first closing member abuts or contacts a first end of a central member, and a distal portion of the first end of the central member extends outward past a point of abutment or contact between the closing end of the first closing member and the first end of the central member, a second closing member is pivotally engaged to a second end of the second arm of the base portion to form a second holding region configured to hold one or more intravenous fluid bags, wherein a closing end of the second closing member abuts or contacts a second end of the central member; and a distal portion of the second end of the central member extends outward past a point of abutment or contact between the closing end of the second closing member and the second end of the central member;

an upper portion of the handle forms an axle;

the handle rotates relative to the double-sided carabiner; and wherein a back side of the axle of the handle includes protuberances, and wherein the protuberances bias the handle to remain in the delayed position.

\* \* \* \* \*